United States Patent
Nishimura

(10) Patent No.: US 9,832,435 B2
(45) Date of Patent: Nov. 28, 2017

(54) OPTICAL SCANNING IMAGE FORMING APPARATUS AND OPTICAL SCANNING IMAGE FORMING METHOD

(71) Applicant: OLYMPUS CORPORATION, Tokyo (JP)

(72) Inventor: Junichi Nishimura, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/298,381

(22) Filed: Oct. 20, 2016

(65) Prior Publication Data

US 2017/0041577 A1    Feb. 9, 2017

Related U.S. Application Data

(63) Continuation of application No. PCT/JP2015/001921, filed on Apr. 6, 2015.

(30) Foreign Application Priority Data

Apr. 23, 2014    (JP) .................. 2014-089149

(51) Int. Cl.
*H04N 9/31* (2006.01)
*G02B 23/24* (2006.01)
(Continued)

(52) U.S. Cl.
CPC ....... *H04N 9/3135* (2013.01); *A61B 1/00006* (2013.01); *A61B 1/00172* (2013.01);
(Continued)

(58) Field of Classification Search
CPC .. H04N 9/3135; H04N 9/3155; H04N 9/3185; H04N 2005/2255; H04N 9/31;
(Continued)

(56) References Cited

U.S. PATENT DOCUMENTS

| 2008/0165360 A1 | 7/2008 | Johnston |
| 2014/0022365 A1 | 1/2014 | Yoshino |

(Continued)

FOREIGN PATENT DOCUMENTS

| JP | 2008-514342 A | 5/2008 |
| JP | 2010-515947 A | 5/2010 |

(Continued)

OTHER PUBLICATIONS

International Search Report dated Jun. 16, 2015 issued in PCT/JP2015/001921.
English Abstract of WO 2006/041452 A1, dated Apr. 20, 2006.

*Primary Examiner* — Sherrie Hsia
(74) *Attorney, Agent, or Firm* — Scully, Scott, Murphy & Presser, P.C.

(57) ABSTRACT

An optical scanning image forming apparatus includes: a light source section; an illumination scanning section; a light detection section; a calculation section calculating a drive waveform for providing a illumination light scanning pattern; and an image drawing section drawing an image, based on detection light detected by the light detection section and image construction coordinates, the calculation section providing different light scanning patterns to the illumination scanning section and calculating distortion correction data, based on comparison between data on the detection lights detected when scanned in the different scanning patterns. An optical scanning image forming method includes: providing different light scanning patterns to an illumination scanning section which scans the illumination light from a light source section to irradiate an object with the illumination light; and calculating distortion correction data, based on comparison between data on the detection light detected when scanned in the different scanning patterns.

17 Claims, 14 Drawing Sheets

(51) Int. Cl.
    *G02B 23/26*     (2006.01)
    *G02B 26/10*     (2006.01)
    *A61B 1/00*     (2006.01)
    *A61B 1/07*     (2006.01)

(52) U.S. Cl.
    CPC ............... *A61B 1/07* (2013.01); *G02B 23/24* (2013.01); *G02B 23/26* (2013.01); *G02B 26/10* (2013.01); *H04N 9/3155* (2013.01); *H04N 9/3185* (2013.01)

(58) Field of Classification Search
    CPC ... A61B 1/00006; A61B 1/00172; A61B 1/07; G02B 23/24; G02B 23/26; G02B 26/10
    USPC .................. 348/65, 67, 68; 382/128, 275
    See application file for complete search history.

(56) References Cited

U.S. PATENT DOCUMENTS

2014/0210975 A1*   7/2014   Hirakawa .......... A61B 1/00172
                                                    348/68
2015/0331229 A1*   11/2015   Nishimura ............. G02B 23/26
                                                   250/227.14

FOREIGN PATENT DOCUMENTS

| JP | 2012-152244 A | 8/2012 |
| --- | --- | --- |
| JP | 5469280 B1 | 4/2014 |

* cited by examiner

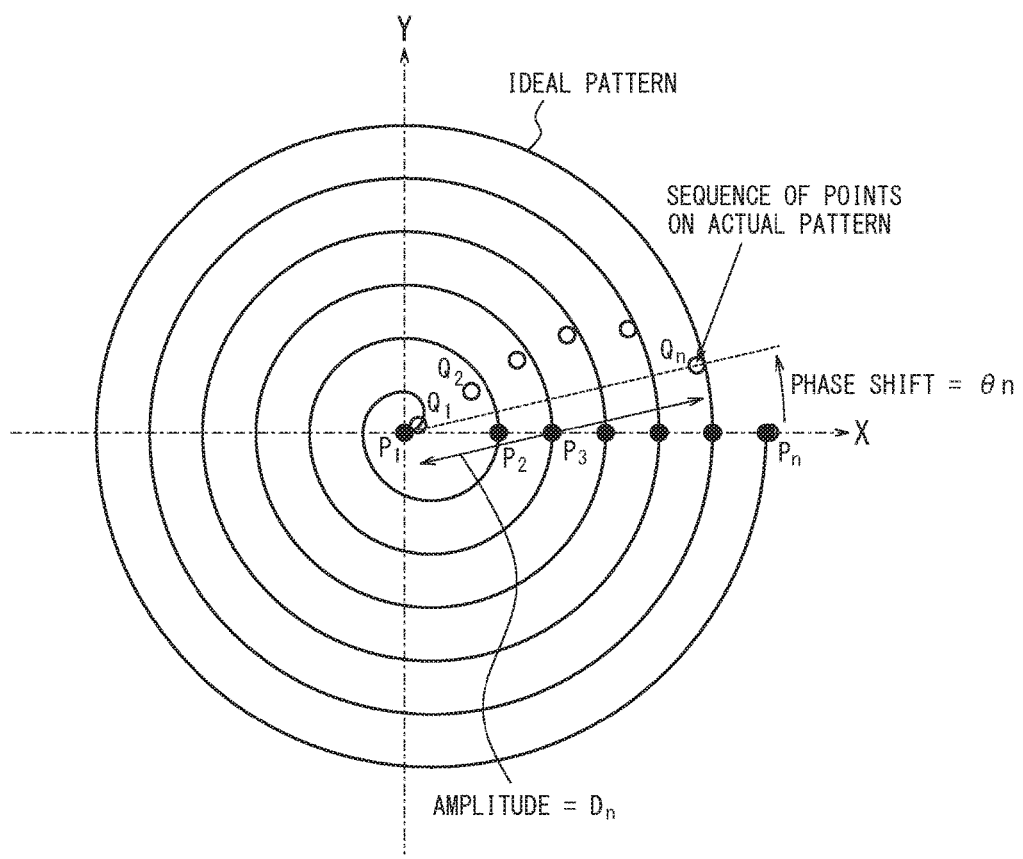

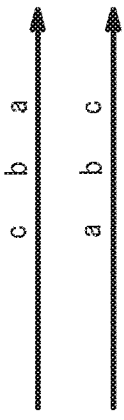
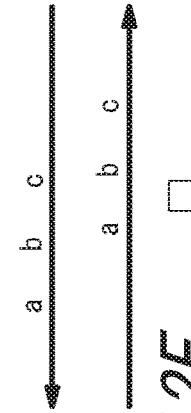
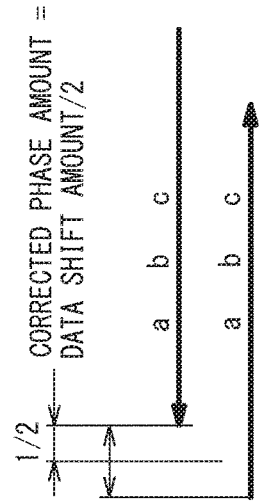
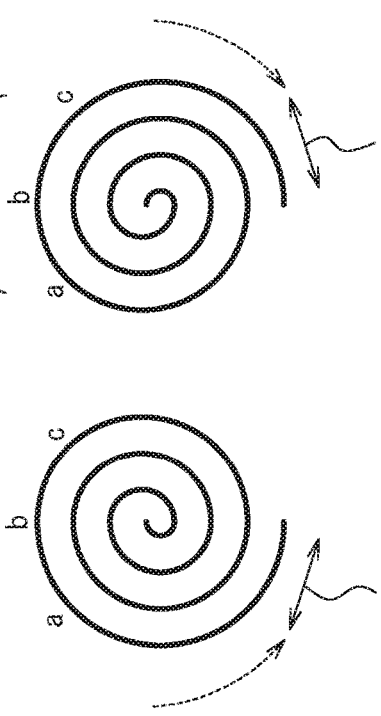
FIG. 12A  FIG. 12B  FIG. 12C  FIG. 12D  FIG. 12E

OPTICAL SCANNING IMAGE FORMING APPARATUS AND OPTICAL SCANNING IMAGE FORMING METHOD

CROSS REFERENCE TO RELATED APPLICATIONS

The present application claims priority from Japanese Patent Application No. 2014-089149 filed on Apr. 23, 2014, the entire disclosure of this earlier application being incorporated herein by reference.

TECHNICAL FIELD

The present disclosure relates to an optical scanning image forming apparatus and an optical scanning image forming method.

BACKGROUND ART

There has been hitherto known an optical scanning-type image forming apparatus which scans illumination light from the tip part of an optical fiber toward an object and detects detection light reflected and scattered by the object or fluorescence generated in the object. In such apparatus, the optical fiber is held in part with the tip part for emitting the illumination light being oscillatable, and an actuator is disposed in the vicinity of the supporting part, so as to vibrate the optical fiber, to thereby scan the detection light on the object.

Optical fibers are not always constant in its properties (such as Young's modulus and density), and susceptible to aging due to ambient environmental change such as temperature change, aging of the constituent members, and impact between an object during use. Members such as actuators including piezoelectric elements and adhesives forming the drive mechanism also vary in property with time. Such aging of properties of the optical fiber and the drive mechanism affects resonance frequency at the leading end of the optical fiber, attenuation coefficient (Q value) of the vibration, and the driving force of the drive mechanism, with the result that the scanning pattern of the optical fiber will deviate from the scanning pattern originally intended, as will be explained in detail with reference to FIGS. 1 and 2.

FIG. 1 illustrate, as a simplified example, the scanning of optical fibers along a circular pattern, in which: FIG. 1A shows a pattern of an optical fiber tip in the X-direction; FIG. 1B shows a pattern of an optical fiber tip in the Y-direction; and FIG. 1C shows an optical scanning pattern in the XY plane. The vibration of the fiber tip in the X-direction is different in phase by 90 degrees from the vibration of the fiber tip in the Y-direction, and thus the fiber tip renders a circular pattern. Meanwhile, FIG. 2 illustrate the scanning of the optical fiber after deterioration with age. Variations in resonance frequency, Q value of the vibration, and driving force of the drive mechanism affect the phase and amplitude, as can be seen in the pattern of the fiber tip in the X-direction and Y-direction of FIGS. 2A and 2B. As a result, the pattern of optical scanning on the object is also deformed as illustrated in FIG. 2C.

Without being limited to the aforementioned case of circular pattern, a scanning pattern 101 in a spiral scan, for example, is also deformed as illustrated by the solid line of FIG. 3, from a pattern (broken line) 102 originally intended. In a case where the pattern of optical scanning has been changed as described above, the resulting image of the object will suffer distortion to be different from the actual object when the image has been generated by mapping pixel data on a two-dimensional coordinates based on the pattern of the optical fiber originally anticipated. More specifically, as illustrated in FIG. 4, the actual pattern (plotted by white circles at certain time intervals) will be deviated in amplitude and phase from an ideal pattern (plotted by black circles at certain time intervals). In particular, when a phase difference θn is generated, the original image shown in FIG. 5A will be formed as an image circumferentially distorted in the center as shown in FIG. 5B.

To overcome such problem, JP2008514342A (Patent Literature (PTL) 1) illustrates the use of a scanning position detecting means such as position sensor devices (PSD), so as to obtain coordinate values of the actual scanning pattern and create a lookup table having information on the coordinate values, to thereby correct the coordinate to be applied to the pixels based on the lookup table.

Further, US20080165360 (PTL 2) suggests, as a method of correcting image distortion using a reflection image, storing a specific reference chart in a memory or the like and comparing the reference chart with a scanning pattern actually obtained.

CITATION LIST

Patent Literature

PTL 1: JP2008514342A
PTL 2: US20080165360

SUMMARY

The disclosed optical scanning image forming apparatus includes: a light source section; an illumination scanning section scanning illumination light from the light source section and irradiating the illumination light onto an object; a light detection section detecting detection light from the object; a calculation section calculating: a drive waveform for providing a light scanning pattern to be formed by the illumination scanning section; and image construction coordinates; and an image drawing section drawing an image based on the detection light detected by the light detection section and the image construction coordinates, in which the calculation section provides a plurality of different light scanning patterns to the illumination scanning section, and compares between data on the detection light detected by the light detection section when the illumination light has been scanned in the plurality of different scanning patterns, to thereby calculate distortion correction data.

Further, in the disclosed optical scanning image forming apparatus, the plurality of different light scanning patterns may preferably be different in light scanning direction.

Here, in the disclosed optical scanning image forming apparatus, the plurality of different light scanning patterns may preferably have portions opposite in scanning direction of the illumination light.

Here, "opposite in scanning direction of the illumination light" refers to a relation which generates images that are distorted in mutually opposite directions after the image formation.

Further, in the disclosed optical scanning image forming apparatus, the plurality of different light scanning patterns each may preferably be in a spiral shape and include two scanning patterns having distortions mutually opposite in the rotational direction.

In this case, the calculation section may preferably compare between data of the detection light detected by the light detection section when the illumination light has been scanned in the two scanning patterns, to thereby calculate distortion correction data.

In the aforementioned case, the calculation section may preferably take out data sequences of the detection light detected by the light detection section for a certain period when the illumination light has been scanned in the two scanning patterns, and align the two data sequences with one of the data sequences that has been obtained for one of the two scanning patterns being converted in an opposite direction and aligned such that the difference between the converted data sequence and the data sequence of the illumination light scanned in the other scanning pattern are minimized, to thereby calculate the distortion correction data based on comparison between the two data sequences.

Furthermore, in the disclosed optical scanning image forming apparatus, the image drawing section may preferably use the distortion correction data to correct, in the scanning of the illumination light after the distortion correction data has been calculated, data on the detection light detected by the light detection section, and draw an image.

Further, in the disclosed optical scanning image forming apparatus, the plurality of different scanning patterns may preferably be raster scans and use scanning patterns mutually opposite in a fast axis direction.

In addition, the disclosed optical scanning image forming apparatus may preferably be applied to an optical scanning endoscope.

Here, the disclosed optical scanning image forming method includes the steps of:

providing a plurality of different light scanning patterns to an illumination scanning section which scans the illumination light from a light source section to irradiate an object with the illumination light; and causing a calculation section to calculate distortion correction data based on comparison between data on the detection light detected by a light detection section when the illumination light has been scanned in the plurality of different scanning patterns.

Further, in the disclosed optical scanning image forming method, the plurality of different light scanning patterns may preferably be different in the scanning direction of the illumination light.

Further, in the disclosed optical scanning image forming method, the plurality of different light scanning patterns may preferably have a portion opposite in scanning direction of the illumination light.

Further, in the disclosed optical scanning image forming method, the plurality of different scanning patterns each may preferably be in a spiral shape, and include two scanning patterns mutually opposite in distortion in the rotational direction.

In this case, the calculation section may preferably calculate distortion correction data based on comparison between data on the detection light detected by the light detection section, when the illumination light has been scanned in the two scanning patterns.

Further, in the aforementioned case, the distortion correction data may preferably be a data sequence for each round of a spiral scanning pattern.

Further, in the aforementioned case, the calculation section may preferably take out data sequences of the detection light detected by the light detection section for a certain period when the illumination light has been scanned in the two scanning patterns, and align the two data sequences with one of the data sequences that has been obtained for one of the two scanning patterns being converted in an opposite direction and aligned such that the difference between the converted data sequence and the data sequence of the illumination light scanned in the other scanning pattern are minimized, to thereby calculate the distortion correction data based on comparison between the two data sequences.

Still further, the disclosed optical scanning image forming method may preferably further include, in scanning of the illumination light after the step of calculating the distortion correction data, the step of causing the image drawing section to use the distortion correction data to correct data on the detection light detected by the light detection section, and to draw an image.

In addition, in the disclosed optical scanning image forming method, the plurality of different scanning patterns may preferably be raster scans, and use scanning patterns mutually opposite in a fast axis direction.

BRIEF DESCRIPTION OF DRAWINGS

In the accompanying drawings:

FIGS. 1A-1C are diagrams illustrating the scanning of optical fibers along a circular pattern, in which: FIG. 1A shows a pattern of an optical fiber tip in the X-direction; FIG. 1B shows a pattern of an optical fiber tip in the Y-direction; and FIG. 1C shows an optical scanning pattern in the XY plane;

FIGS. 2A-2C illustrate an exemplary deformation over time of the scanning pattern of FIG. 1, in which: FIG. 2A shows a pattern of an optical fiber tip in the X-direction; FIG. 2B shows a pattern of an optical fiber tip in the Y-direction; and FIG. 2C shows an optical scanning pattern in the XY plane;

FIG. 4 is a diagram for illustrating an amplitude and phase shift;

FIGS. 12A and 12B show two spiral scanning patterns mutually opposite in distortion in the rotational direction;

FIG. 12C shows data sequences of detection light detected by the light detection section over a certain period, when illumination light has been scanned in the two scanning patterns of FIGS. 12A and 12B;

FIG. 12D shows data sequences of illumination light, with one scanned in one of the two scanning patterns of FIG. 12C having been converted in the opposite direction and aligned;

FIG. 12E shows the two data sequences of FIG. 12D which are aligned such that the difference between the two data sequences of illumination light of FIG. 12D can be reduced to minimum;

DESCRIPTION OF EMBODIMENTS

The following describes an embodiment of the disclosed apparatus and method, with reference to the drawings.

Optical Scanning Image Forming Apparatus

Figure 1A:
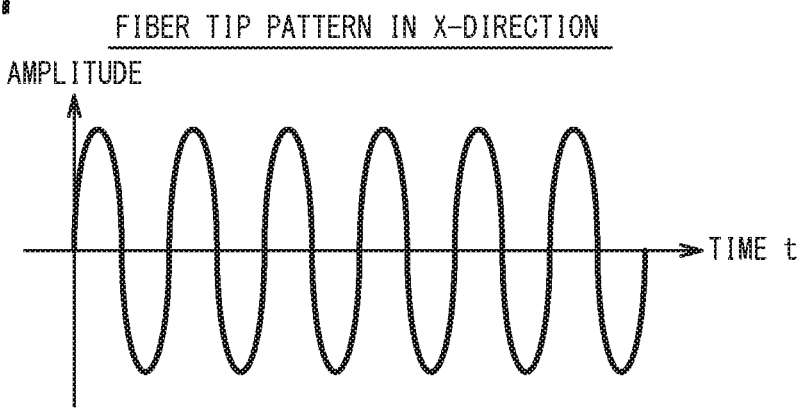
Figure 1B:
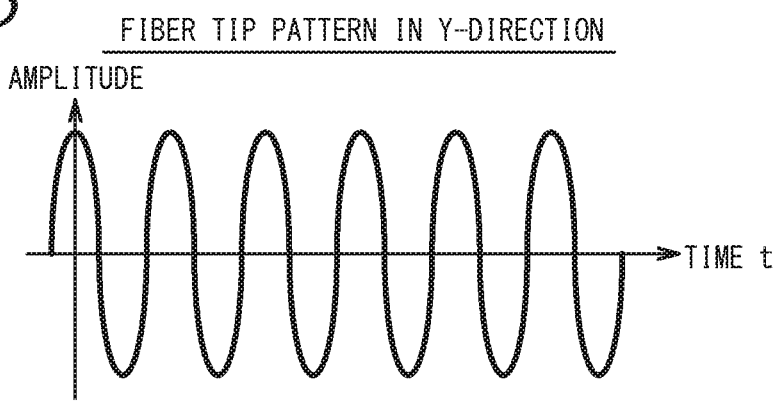
Figure 1C:
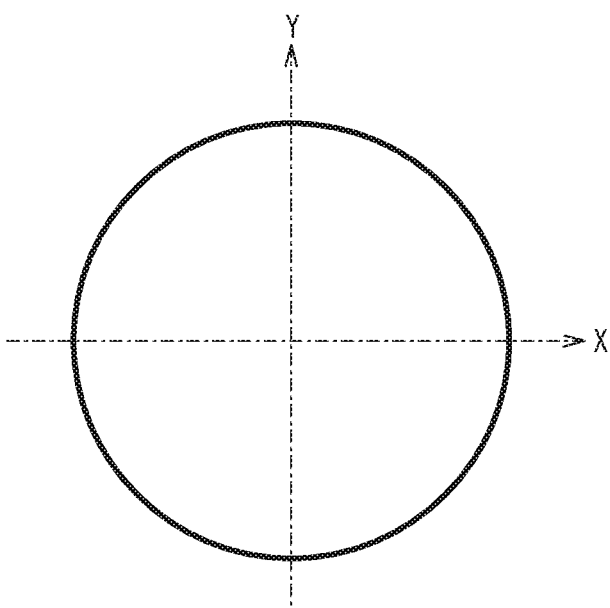
Figure 2A:
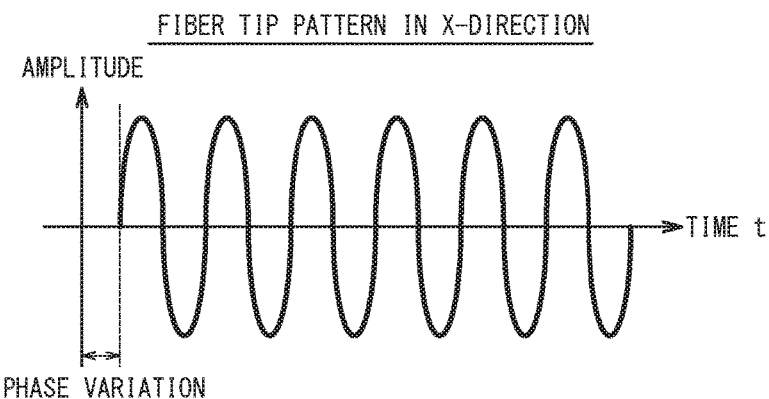
Figure 2B:
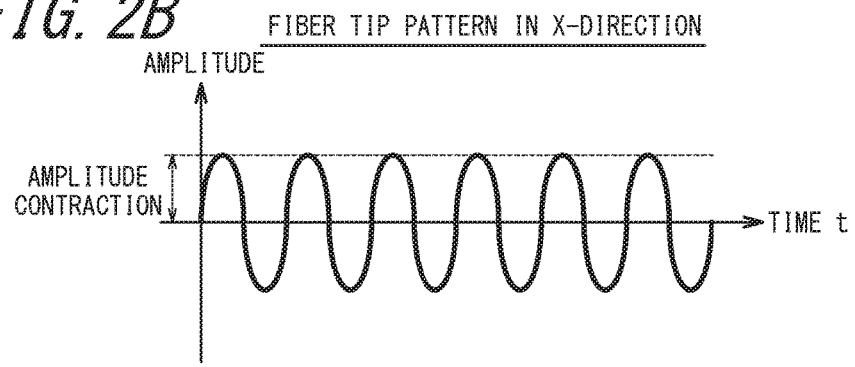
Figure 2C:
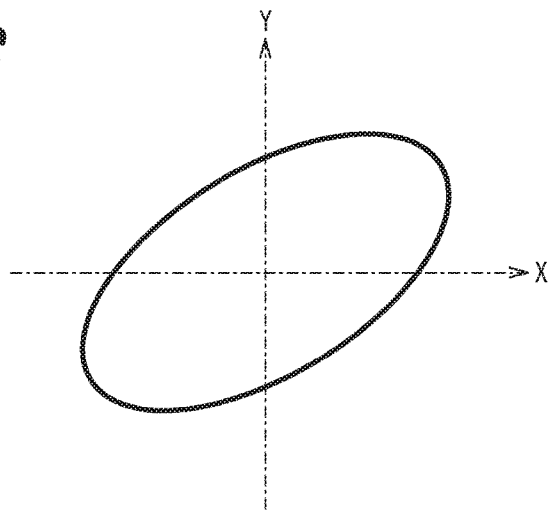
Figure 3:
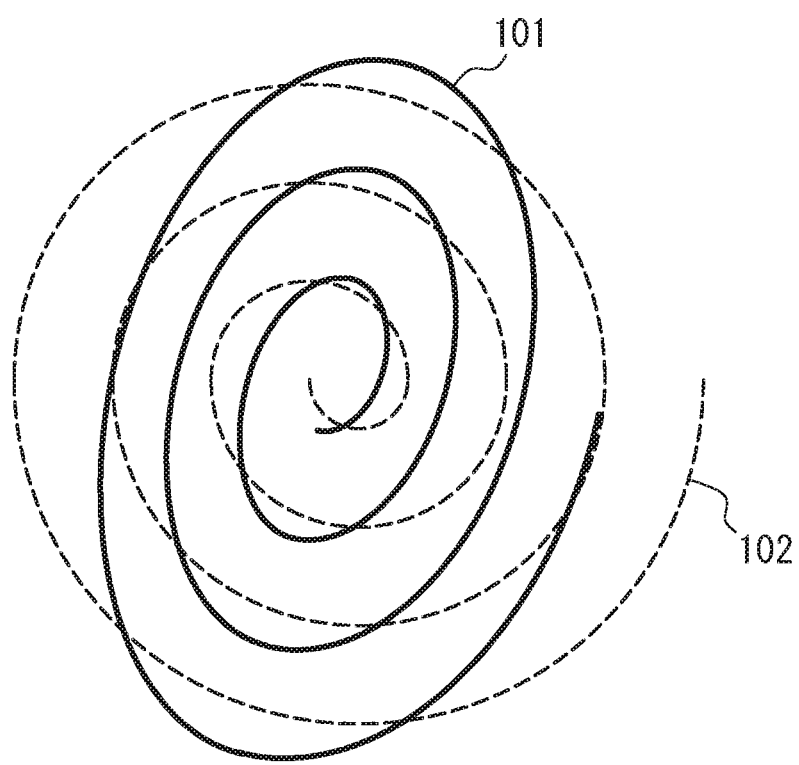
FIG. 3 illustrates an example of a deformed spiral scanning pattern.
Figure 5A:
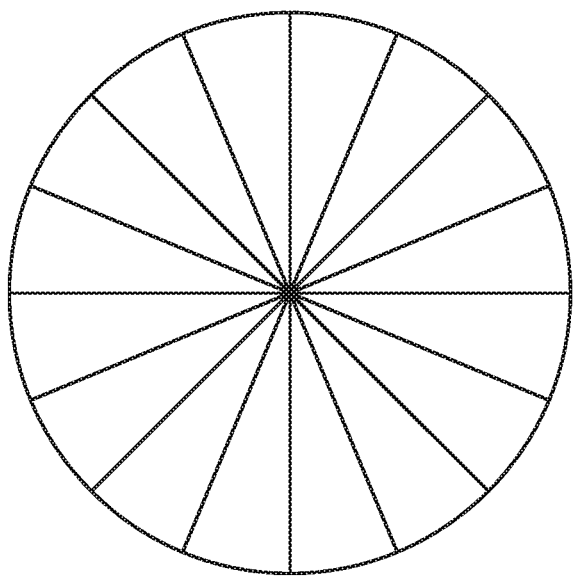
FIG. 5A is a schematic diagram illustrating an original image.
Figure 5B:
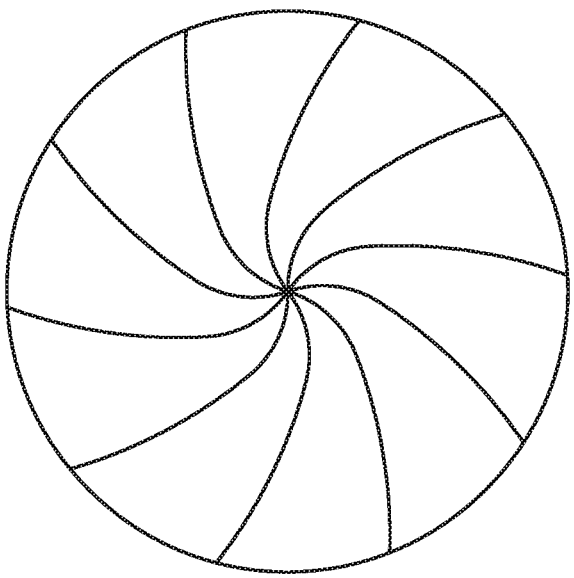
FIG. 5B is a schematic diagram illustrating an image distorted at the center.
Figure 6:
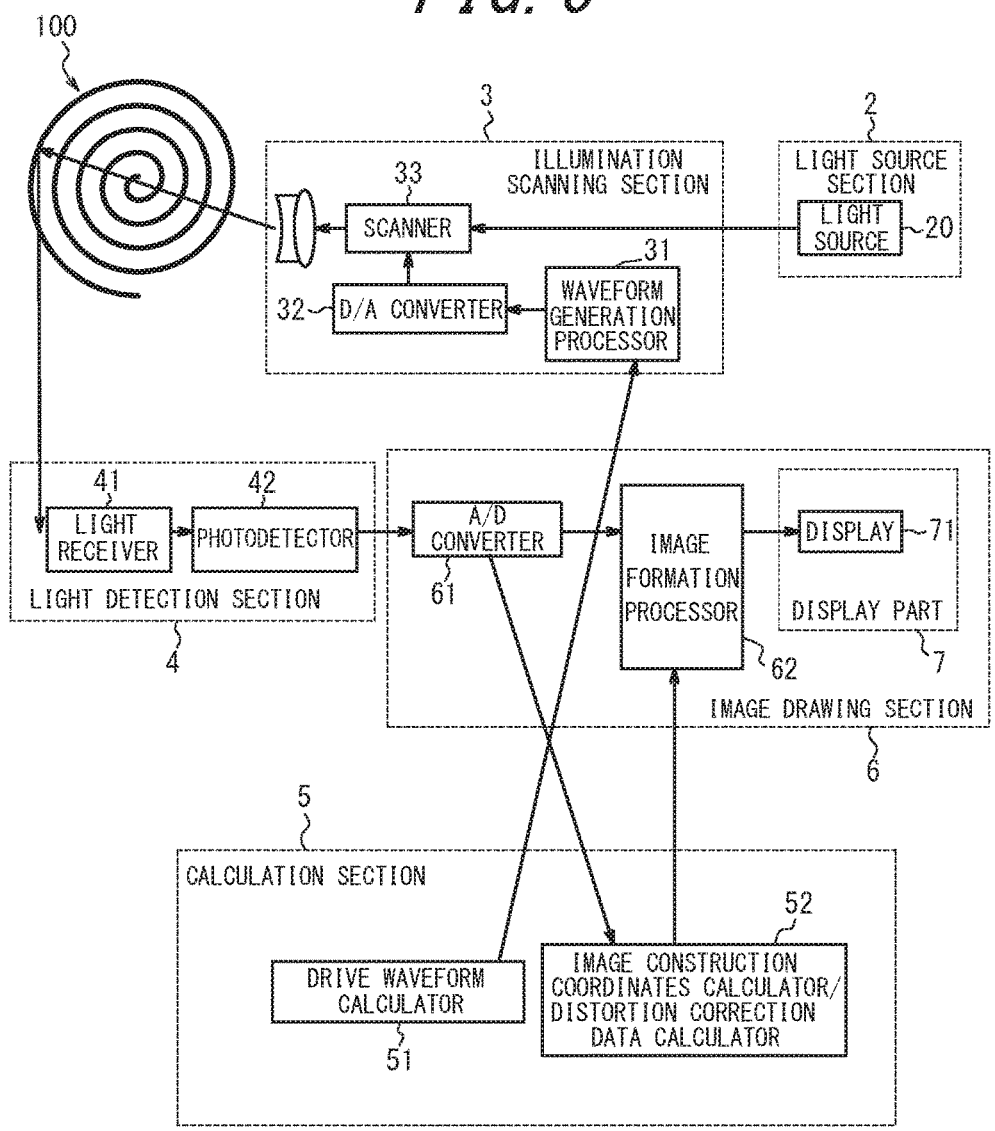
FIG. 6 is a block diagram of an embodiment of the disclosed optical scanning image forming apparatus.

FIG. 6 is a block diagram of an embodiment of the disclosed optical scanning image forming apparatus (endoscope apparatus). As illustrated in FIG. 6, the optical scanning image forming apparatus 1 includes: a light source section 2; an illumination scanning section 3 scanning illumination light from the light source section 2 and irradiating the illumination light onto an object; a light detection section 4 detecting detection light from the object; a calculation section 5 for calculating a drive waveform for providing a light scanning pattern to the illumination scanning section 3 and image construction coordinates; an image drawing section 6 drawing an image based on the detection light detected by the light detection section 4 and the image construction coordinates; and a display part 7.

The light source section 2 has a light source 20, and multiplexes lights from, for example, three laser light sources emitting continuous wave (CW) laser lights of three primary colors of red, green, and blue, so as to emit the multiplexed light as white light. Examples for use as the laser light sources may include, for example, a diode pumped solid state (DPSS) laser and a laser diode. Needless to say, the light source 20 may employ one laser light source or a plurality of other light sources, without being limited to the aforementioned configuration.

Figure 7:
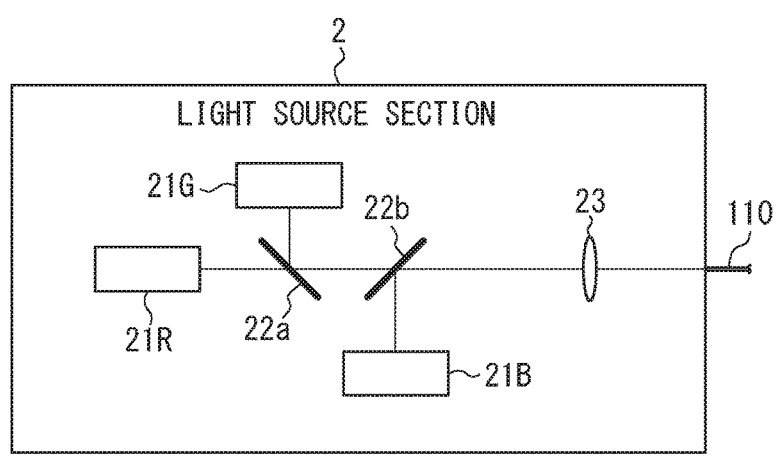
FIG. 7 is a diagram illustrating a schematic configuration of the light source section.

FIG. 7 is a diagram illustrating a schematic configuration of the light source section 2. The light source section 2 includes laser light sources 21R, 21G, 21B emitting continuous wave (CW) of three primary colors of red, green, and blue; dichroic mirrors 22a, 22b; and a lens 23. The red laser light source 21R may employ, for example, a semiconductor laser (laser diode (LD)). The green laser light source 21G may employ a diode pumped solid state (DPSS) laser. The blue laser light source 21B may employ, for example, a laser diode (LD).

A red laser light emitted from the laser light source 21R emits a red laser light, which sequentially passes through the dichroic mirror 22a and the dichroic mirror 22b. The laser light source 21G emits green laser light, which is reflected by the dichroic mirror 22a and coaxially multiplexed with the red laser light so as to pass through the dichroic mirror 22b. The laser light source 21B emits blue laser light, which is reflected by the dichroic mirror 22b, and coaxially multiplexed with red laser light and green laser light. In this manner, the dichroic mirror 22b emits white laser light obtained by multiplexing laser lights of three primary colors of red, green, blue.

The laser light sources 21R, 21G, 21B and the dichroic mirrors 22a, 22b are not be limitedly configured as in FIG. 7, and may be configured, for example, to first multiplex green and blue laser lights, which may then be multiplexed with red laser light.

Returning to FIG. 6, the illumination scanning section 3 includes: a waveform generation processor 31 generating a drive waveform, based on the calculation results obtained by the calculation section 5; a D/A converter 32 D/A converting the drive waveform; and a scanner 33 scanning illumination light from the light source section 2 to irradiate an object with the illumination light.

Figure 8:
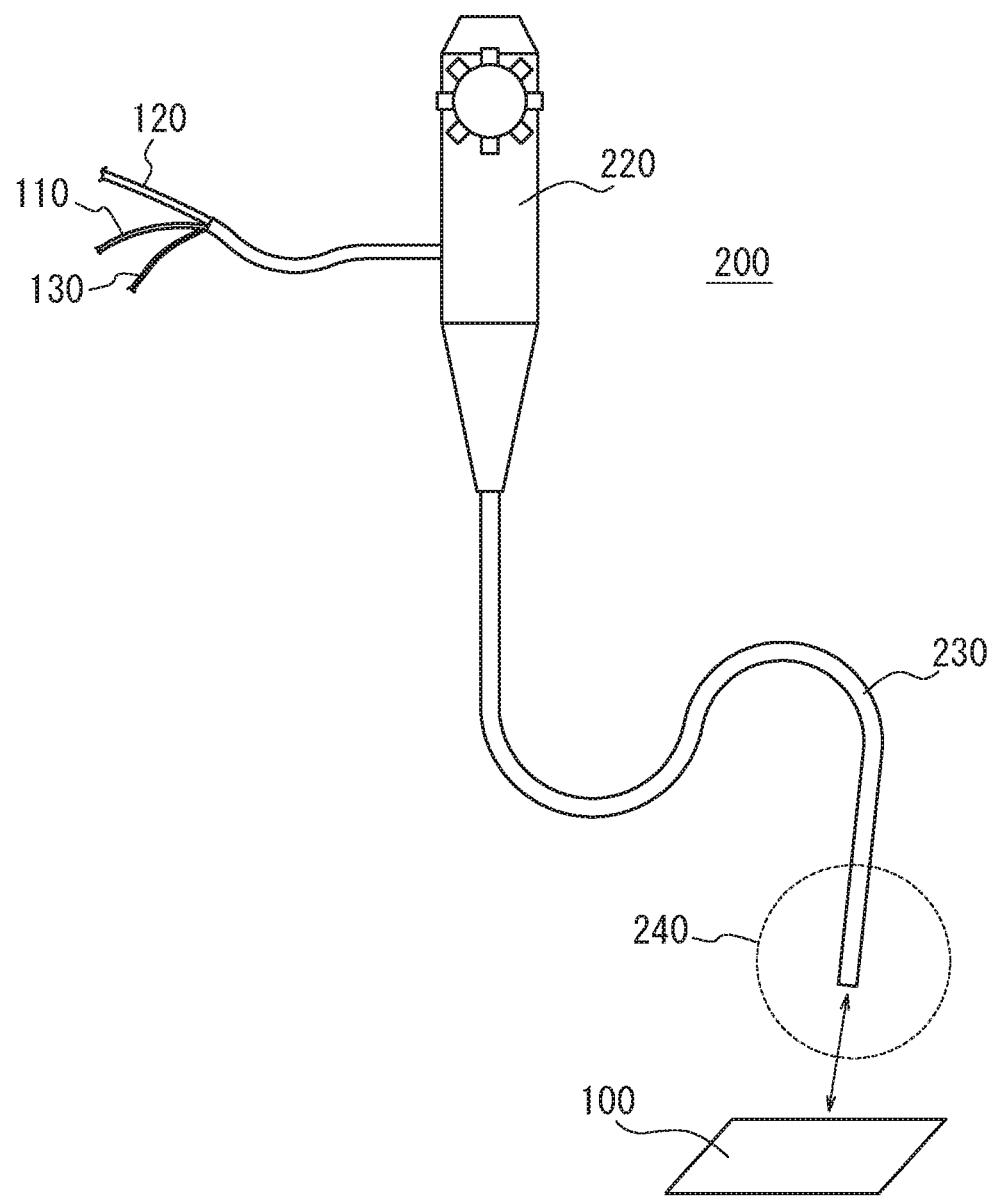
FIG. 8 is a schematic overview of the scope of the optical scanning image forming apparatus.

Here, FIG. 8 is a schematic overview of a scope of an endoscope apparatus. The scanner 33 is disposed at the tip part 240 (enclosed by the dashed line of FIG. 8) of the scope 200. As illustrated in FIG. 8, as an example, the scope 200 includes an operation portion 220 and an insertion portion 230, in which the operation portion 220 is connected at one end thereof to the one end of the insertion portion 230 so as to be integrally formed therewith. The operation portion 220 has an illumination optical fiber 110 from the light source section 2, a detection optical fiber bundle 120 from the detection section 4, and a wiring cable 130 from the D/A converter 32 to the scanner 33 each connected thereto. The illumination optical fiber 110, the detection optical fiber bundle 120, and the wiring cable 130 are guided, through the inside of the insertion portion 230, to a tip part 240, another tip part different from the tip part connected to the operation portion 220 of the insertion portion 230.

Figure 9:
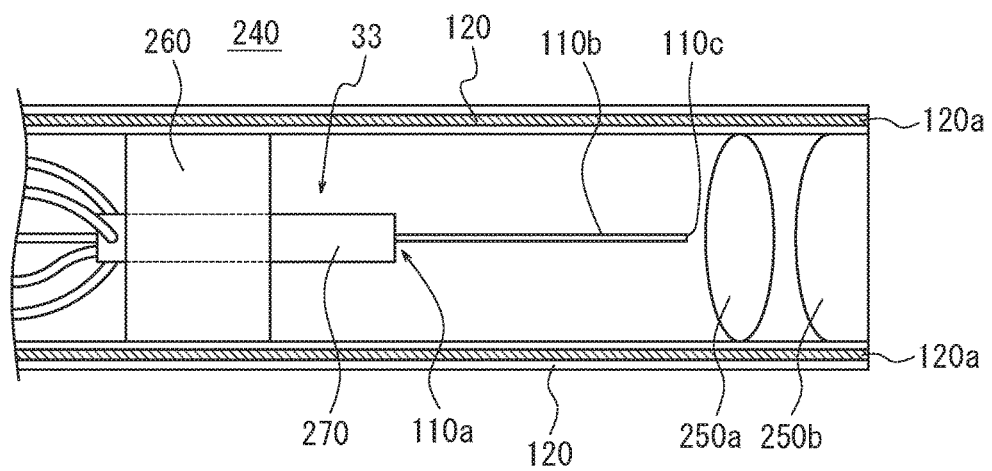
FIG. 9 is a sectional view of the tip part of the scope of the optical scanning image forming apparatus of FIG. 8.

FIG. 9 is an enlarged sectional view of the tip part 240 of the insertion portion 230 of the scope 200 of FIG. 8. The tip part 240 includes: a scanner 33, projection lenses 250a, 250b, and a detection lens (not shown), while having an illumination optical fiber 110 and a detection optical fiber bundle 120 extending through the insertion portion 230.

Figure 10A:
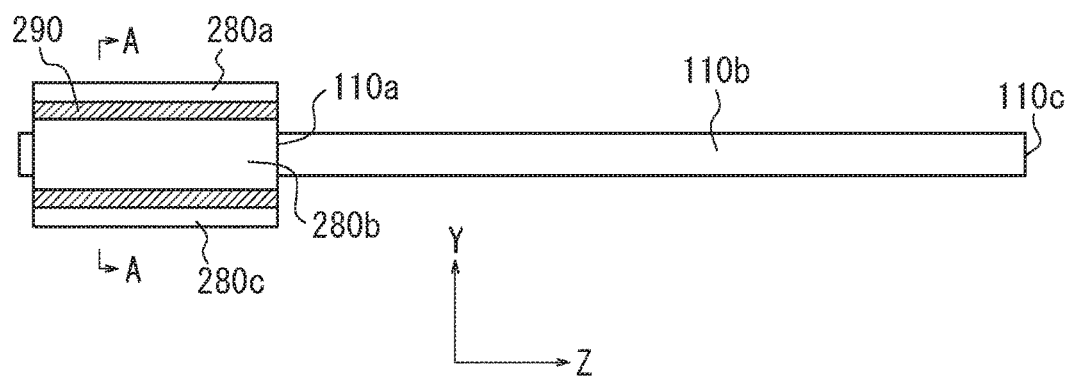
FIG. 10A is a side view of the vibratory drive mechanism of an optical scanning endoscope apparatus and the oscillation part of the illumination optical fiber.
Figure 10B:
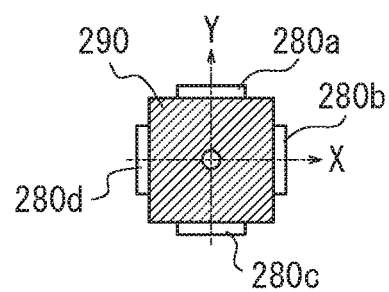
FIG. 10B is a sectional view taken along the line A-A of FIG. 10A.

The scanner 33 is configured by including: an actuator tube 270 fixed inside the insertion portion 230 of the scope 200 via an attachment ring 260; and piezoelectric elements 280a to 280d and a fiber holding member 290 arranged inside the actuator tube 270 (see FIGS. 10A and 10B). The illumination optical fiber 110, which is supported by the fiber holding member 290, has an oscillation part 110b oscillatably supported, the oscillation part 110b being defined between the fixed end 110a supported by the fiber holding member 290 and the tip part 110c. Meanwhile, the detection optical fiber bundle 120 is disposed so as to pass through the circumferential part of the insertion portion 230 to extend to the tip end of the tip part 240.

Further, the projection lenses 250a, 250b and the detection lens are disposed at an extreme tip of the tip part 240. The projection lenses 250a, 250b are configured such that laser light emitted from the tip part 110c of the illumination optical fiber 110 is substantially converged on an observation object 100. Further, the detection lens is disposed to take in the laser light that has been reflected, scattered, and refracted by the object 100 (illumination light that has been interacted with the observation object 100) after being converged on the observation object 100, so as to converge and couple the laser light to the detection optical fiber bundle 120 disposed behind the detection lens. Here, one projection lens or a plurality of other lenses may constitute the projection lens system, without being limited to the two-lens configuration.

FIG. 10A illustrates a vibratory drive mechanism of the optical scanning image forming apparatus 1 and the oscillation part 110b of the illumination optical fiber 110, FIG. 10B is a sectional view taken along the line A-A of FIG. 10A, and FIG. 10C is a sectional view taken along the line B-B of FIG. 10A. The illumination optical fiber 110 penetrates the center of the fiber holding member 290 in a prism shape, so as to be fixed and held by the fiber holding member 290. Accordingly, the illumination optical fiber 110 has a fixed part thereof penetrating the fiber holding member 290. The fiber holding member 290 has four side faces each facing the +Y direction and the +X direction and the directions opposite thereto, respectively. Then, the fiber holding member 290 has, in the +Y and −Y directions, a pair of the Y-direction driving piezoelectric elements 280a, 280c fixed thereon, while having, in the +X and −X directions, a pair of the X-direction driving piezoelectric elements 280b, 280d fixed thereon.

The piezoelectric elements 280a to 280d are each connected with the wiring cable 130. A drive voltage generator applies voltages to the X-direction driving piezoelectric elements 280b, 280d and to the Y-direction driving piezoelectric elements 280a, 280c at independently different driving frequencies, to thereby vibratory drive the piezoelectric elements. When the Y-direction driving piezoelectric elements 280a, 280c and the X-direction driving piezoelectric elements 280b, 280d are each vibratory driven, the oscillation part 110b of the illumination optical fiber 110 is vibrated and the tip part 110c is deflected, and thus, laser light emitted from the tip part 110c sequentially scans the surface of the observation object 100.

Returning to FIG. 6, the light detection section 4 has a light receiver 41 receiving detection light reflected/scattered by the object or detection light such as fluorescence generated by the object, and a photodetector 42 detecting the received detection light. For example, the photodetector 42 decomposes signal light transmitted through the optical fiber bundle 120 into its spectral components, and photoelectrically converts the decomposed signal light.

Figure 11:
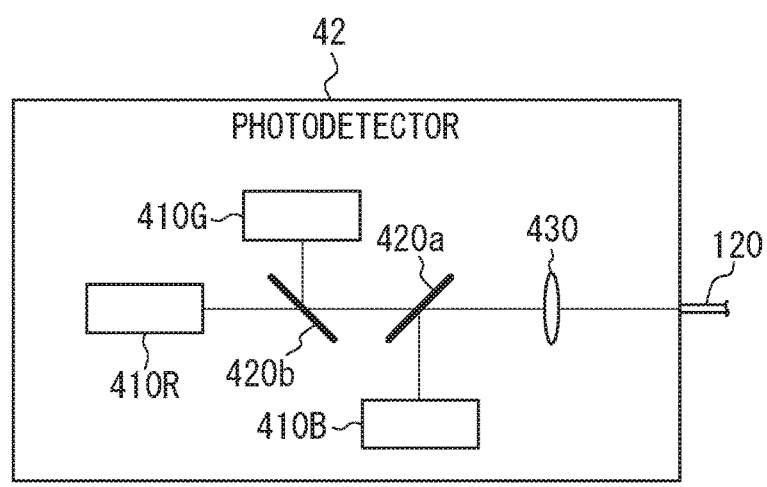
FIG. 11 illustrates a schematic configuration of the photodetector.

FIG. 11 illustrates a schematic configuration of the photodetector 42. The photodetector 42 includes: light receivers 410R, 410G, 410B for detecting light corresponding to each color of red, green, or blue; dichroic mirrors 420a, 420b; and a lens 430. The optical fiber bundle 120 is connected to the photodetector 42.

The lens 430 converts signal light emitted from an emitting end of the optical fiber bundle 120 into substantially parallel light fluxes, of which light in the wavelength range of blue is reflected and separated by the dichroic mirror 420a while lights in the wavelength ranges of red and green pass through the dichroic mirror 420a. The light in the wavelength range of blue separated by the dichroic mirror 420a is received by the light receiver 410B and photoelectrically converted. The lights in the wavelength ranges of red and green that have passed through the dichroic mirror 420a are separated by the dichroic mirror 420b which reflects light in the wavelength range of green while transmitting light in the wavelength range of red. The green and red signal lights separated by the dichroic mirror 420b are each received by the light receiver 410G and the light receiver 410R, respectively, and photoelectrically converted.

The photoelectrically-converted outputs from the light receivers 410R, 410G, and 410B are input to the image drawing section 6. Here, the light receivers 410R, 410G, 410B and the dichroic mirrors 420a, 420b may be arranged, without being limited to the configuration of FIG. 7, so as to separate, for example, a red light from the signal light, and then further to separate green and blue lights.

Returning again to FIG. 6, the calculation section 5 includes: a drive waveform calculator 51 capable of setting basic parameters to be given to actuators such as the piezoelectric elements 280a to 280d such as drive frequency, period, and the number of frames per 1 period of the drive waveform; and an image construction coordinates calculator/distortion correction data calculator 52 calculating, based on the set parameters, a drive waveform and image construction coordinates. Then, the drive waveform thus calculated is sent to the waveform generation processor 31 of the illumination scanning section 3, and given a light scanning pattern to be formed by the illumination scanning section 3. Here, in this embodiment, the drive waveform calculated by the calculation section 5 has a feature in that the period is 1 second, and the period has a plurality of frames of different phases. The calculated image construction coordinates are sent to the image drawing section 6.

When the optical scanning image forming apparatus 1 is operated for observation, the waveform generation processor 31 is driven under the control of the calculation section 5, so as to apply vibration voltage via the wiring cable 130 to the piezoelectric elements 280a to 280d constituting the scanner 33, to thereby vibrates the oscillation part 110b of the illumination optical fiber 110. In the case of raster scan, for example, the Y-direction driving piezoelectric elements 280a, 280c are vibratory driven, for example, at several kHz which is the resonance frequency in the Y direction of the oscillation part 110b of the illumination optical fiber 110, while the X-direction driving piezoelectric elements 280b, 280d are vibratory driven at a non-resonance frequency of, for example, about 30 Hz, which is considerably slower than the resonance frequency in the Y direction.

Next, as illustrated in FIG. 6, the image drawing section 6 converts detection light detected by the light detection section 4 into a digital signal through an A/D converter 61. Then, information on the digital signal and the image construction coordinates calculated by the calculation section 5 are received by an image formation processor 62, which divides the frames based on the information thus received, allocates the obtained image data to each frame, and displays the image on the display 71 of the display part 7.

Here, in the disclosed optical scanning image forming apparatus according to this embodiment, the calculation section 5 provides a plurality of different scanning patterns of illumination light to the illumination scanning section 3, and calculates distortion correction data, based on comparison between data on detection light detected by the light detection section 4 when illumination light has been scanned in the plurality of different scanning patterns. Specific description thereof is given below with reference to FIGS. 12A to 12E.

As illustrated in FIGS. 12A and 12B, the calculation section 5 in this embodiment provides the illumination scanning section 3 with a plurality of (two in the illustrated example) different light scanning patterns that are different in the scanning direction of illumination light. As illustrated in FIGS. 12A and 12B, these two different light scanning patterns are opposite in scanning direction of illumination light. That is, the two light scanning patterns are each in a spiral shape and include two scanning patterns mutually opposite in distortion in the rotational direction. As illustrated in FIGS. 12A and 12B, points specific to the object are defined. Three points of "a", "b", and "c" are defined in the illustrated example; however, at least one point needs to be defined. The points are positioned where the different scanning patterns commonly pass through to irradiate with illumination light, as illustrated in FIGS. 12A and 12B.

In this embodiment, the image construction coordinates calculator/distortion correction data calculator 52 of the calculation section 5 calculates, based on comparison between data on detection light detected by the light detection section 4 when illumination light is scanned in the two scanning patterns illustrated in FIGS. 12A and 12B.

Specifically, the calculation section 5 takes out data sequences of detection light detected by the light detection section 4 for a certain period (for example, the period of the drive waveform) when illumination light has been scanned in the two scanning patterns of FIGS. 12A and 12B (see FIG. 12C), and aligns the two data sequences with one (the upper data sequence of FIG. 12C) of the data sequences that has been obtained for one of the two scanning patterns being converted in an opposite direction and aligned (see FIG. 12D) such that the difference between the converted data sequence and the data sequence of illumination light scanned in the other scanning pattern (see FIG. 12E) are minimized, to thereby calculate the distortion correction data based on comparison between the two data sequences. Here, a least square method may be exemplified as a method available for aligning the two data sequences in such a manner as to minimize the difference between the converted data sequence and the other data string of illumination light scanned in the other scanning pattern, as illustrated in FIG. 12E.

Here, as illustrated in FIGS. 12A and 12B, the scanning pattern of illumination light may have a phase shift resulting from mechanical phase delay of the fiber. However, in this embodiment, the two scanning patterns of illumination light shown in FIGS. 12A and 12B are different from each other; specifically, the two different light scanning patterns are each in a spiral shape opposite in scanning direction of illumination light and have distortions in the rotational direction mutually opposite to each other.

Accordingly, the phase shifts become mutually opposite to each other, and thus, when the two data sequences are aligned as illustrated in FIG. 12E, an ideal data shift amount should be twice the phase shift amount. Thus, the data shift amount may be obtained for the two data sequences which are aligned as illustrated in FIG. 12E, to thereby calculate the phase shift, which allows for calculating distortion correction data. In other words, the data shift amount multiplied by ½ may be obtained as the phase shift amount.

The phase shift amount may be calculated as described above for each different round of the spiral scan (i.e., for each different radius), to thereby obtain a plurality of phase shift amounts.

The distortion correction data calculated for each round is transmitted from the image construction coordinates calculator/distortion correction data calculator 52 of the calculation section 5 to the image formation processor 62 of the image drawing section 6, allowing the image formation processor 62 of the image drawing section 6 to use, in the scanning of illumination light after the distortion correction data has been calculated, the calculated distortion correction data to correct detection light detected by the light detection section 4 to thereby draw an image.

Accordingly, the disclosed optical scanning image forming apparatus is capable of correcting distortion in images by a simple technique. Further, this embodiment is configured to calculate distortion correction data for each round, which brings advantages in that load in calculation can be reduced as compared to the case of calculating an enormous amount of data present in all the rounds, which is more than expected from simple division of the data for each round, and the control can also be simplified. Further, this embodiment eliminates the need to obtain, by PSD or the like, an actual pattern or a reference chart and store such data in a memory. Further, this embodiment allows for correction as long as a plurality of images can be obtained, and thus, in a case of a scanning endoscope for example, distortion can be corrected with the scanning endoscope being in the test subject. In addition, correction can be made in a use environment, which makes the apparatus to be readily adaptable to environmental changes such as temperature.

Optical Scanning Image Forming Method

Figure 13:
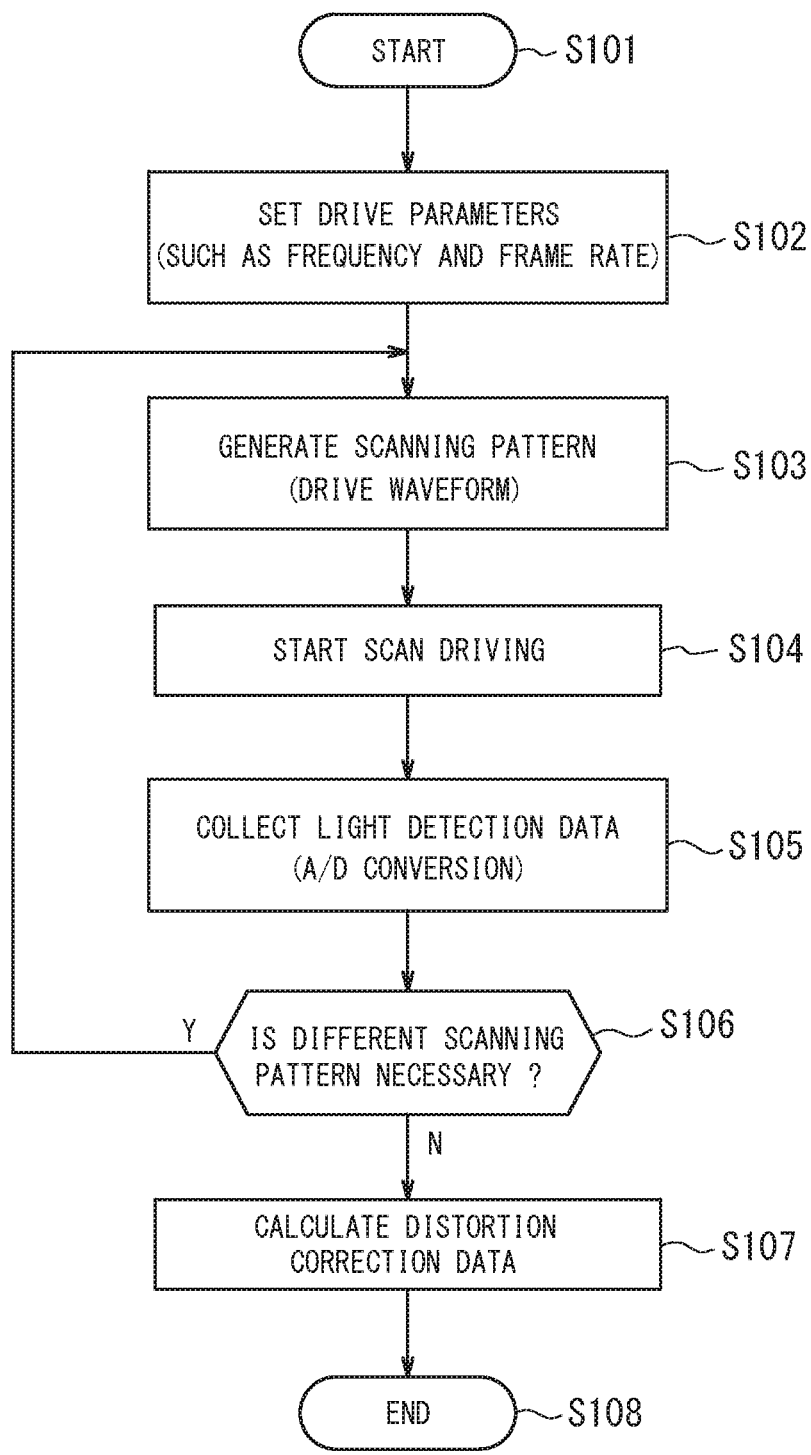
FIG. 13 is a flowchart of an embodiment of the disclosed optical scanning image forming method.
Figure 14:
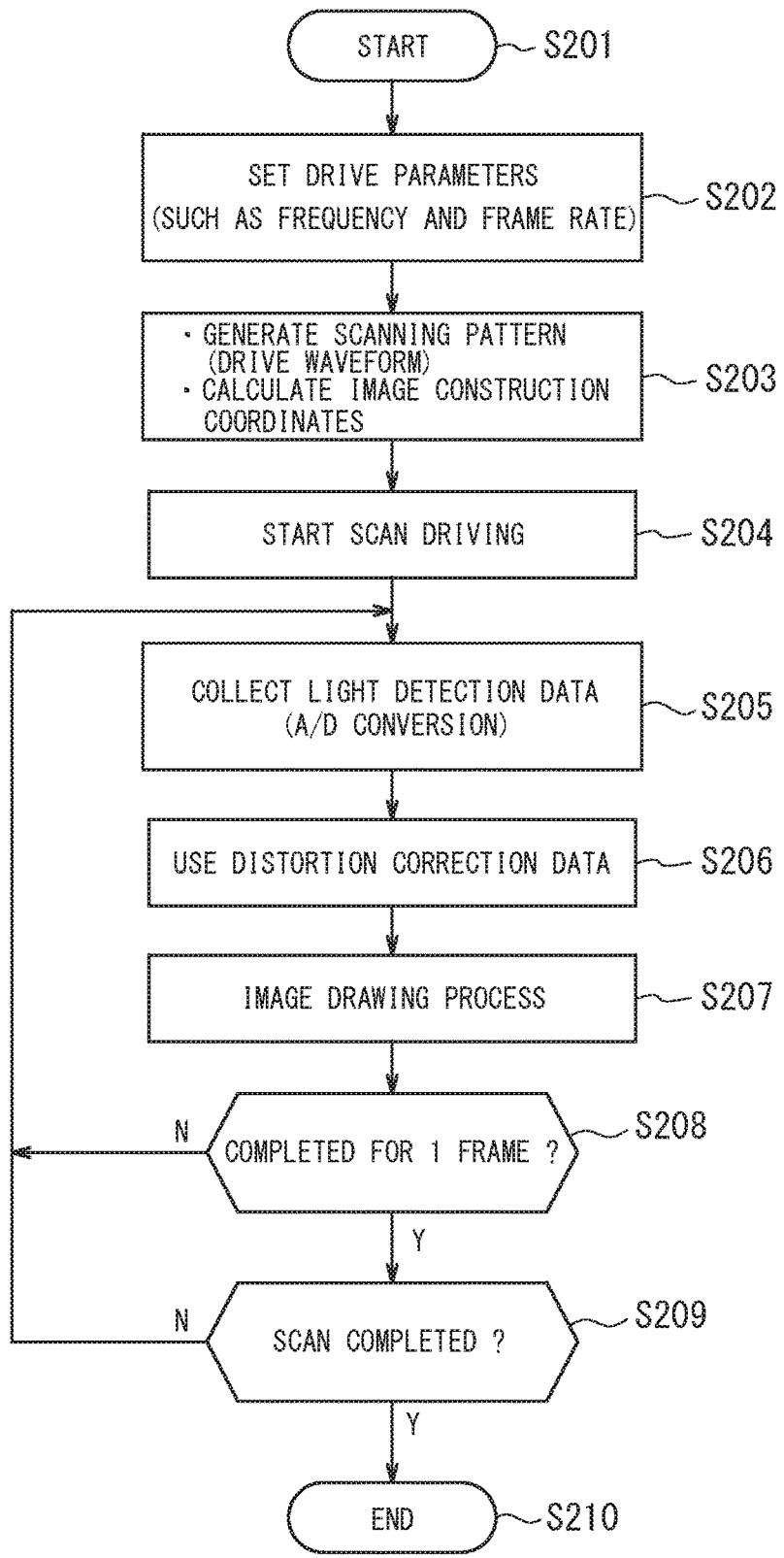
FIG. 14 is a flowchart of the disclosed optical scanning image forming method according to an embodiment.

Next, with reference to FIGS. 13 and 14, an optical scanning image forming method according to an embodiment are described.

First, when the disclosed optical scanning image forming method is started (Step S101), drive parameters of scanning waveform are set (Step S102). This process may be carried out in the drive waveform calculator 51 of the calculation section 5, as illustrated in FIG. 6. The drive parameters may include basic parameters such as drive frequencies and periods of drive waveforms to be given to the actuators of the piezoelectric elements 280a to 280d.

Next, the drive parameters thus set are received by the waveform generation processor 31 of the illumination scanning section 3, which generates a scanning pattern (drive waveform) (Step S103). Then, the scanner 33 starts scan driving according to the scanning pattern (Step S104).

Here, the scan driving for the first round may be in a spiral scanning pattern for example, as illustrated in FIG. 12A.

Next, as illustrated in FIGS. 6 and 13, the photodetector 42 detects detection light received by the light receiver 41 of the light detection section 4, and the A/D converter 61 converts the analog data of the received detection light into digital data to collect light detection data (Step S105).

Then, the calculation section 5 determines whether another scanning pattern is necessary or not (Step S106). Here, the optical scanning image forming method of this embodiment includes the step of providing a plurality of different scanning patterns of illumination light to the illumination scanning section 3 which scans illumination light from the light source section 2 to irradiate an object with the illumination light. Therefore, the process returns to Step S103 because of the need to provide a scanning pattern different from that for the first round. Here, the plurality of different scanning patterns may preferably be different in scanning direction of illumination light as described above, and more preferably include a portion opposite in scanning direction of illumination light.

In the optical scanning image forming method of this embodiment may drive in a scanning pattern in a spiral shape for the second round, as illustrated in FIG. 12B (Step S103). In other words, a plurality of different scanning patterns are defined into two spiral scanning patterns that are mutually opposite in distortion in the rotational direction. Then, similarly to the first round, Steps S104 and S105 above are performed.

In this embodiment, when the two scanning patterns of FIGS. 12A and 12B are used, phase correction can be performed by the method as described above with reference to FIGS. 12C to 12E. Thus, no more different scanning pattern is determined to be necessary (Step S106).

Next, the calculation section 5 calculates distortion correction data based on comparison between data on detection light detected by the light detection section 4 when illumination light has been scanned in a plurality of different scanning patterns (patterns of FIGS. 12A and 12B in the aforementioned example) (Step S107).

To calculate distortion correction data, as mentioned above, the calculation section 5 may preferably take out data sequences of detection light detected by the light detection section 4 for a certain period (for example, the period of the drive waveform) when illumination light has been scanned in the two scanning patterns (the patterns of FIGS. 12A and 12B in the aforementioned example), and align the two data sequences with one of the data sequences that has been obtained for one of the two scanning patterns being converted in an opposite direction and aligned such that the difference between the converted data sequence and the data sequence of illumination light scanned in the other scanning pattern are minimized (by using, for example, a least square method), to thereby calculate the distortion correction data based on comparison between the two data sequences.

For example, as explained with reference to FIG. 12E, the data shift amount when the two data sequences are aligned may be obtained, which may be multiplied by ½ so as to be obtained as the phase shift amount.

The distortion correction data thus calculated is transmitted from the image construction coordinates calculator/distortion correction data calculator 52 of the calculation section 5 to the image formation processor 62 of the image drawing section 6, and stored in a memory.

Next, description is given of the step of drawing an image with reference to FIG. 14, which follows the step of calculating distortion correction data illustrated in FIG. 13.

First, the step of drawing an image is started (Step S201), and drive parameters for the scanning waveform are set (Step S202). This process may be carried out, as described above, in the drive waveform calculator 51 of the calculation section 5 as illustrated in FIG. 6. The drive parameters may include basic parameters such as drive frequencies and periods of drive waveforms to be given to the actuators of the piezoelectric elements 280a to 280d.

Next, the drive parameters thus set are received by the waveform generation processor 31 of the illumination scanning section 3, which generates a scanning pattern (drive waveform) (Step S203). The scanning pattern is prepared at least for one frame. At the same time, the image construction coordinates calculator/distortion correction data calculator 52 of the calculation section 5 calculates image construction coordinates (Step S203). The image construction coordinates thus calculated is transmitted from the image construction coordinates calculator/distortion correction data calculator 52 to the image formation processor 62 of the image drawing section 6. Then, scan driving is started by the scanner 33 in the scanning pattern thus prepared (Step S204).

Next, as illustrated in FIGS. 6 and 13, detection light received by the light receiver 41 of the light detection section 4 is detected by the photodetector 42, and analog data on the received detection light is converted into digital data by the A/D converter 61, to collect light detection data (Step S205).

Then, the image drawing section 6 uses the light detection data and the already-transmitted image construction coordinates and distortion correction data (Step S206), to continuously perform image drawing process for each round, to thereby complete image drawing in one frame (Step S207).

Next, it is determined whether or not the image drawing for one frame, i.e., the correction process of light detection data based on the distortion correction data for all the rounds has been completed (Step S208), and when the image drawing for one frame has not been completed, Steps S205 to S207 above are repeated. When the image drawing for one frame has been completed, it is determined whether the scanning has been completed or not (Step S209). When the scanning has not been completed, Steps S205 to S207 are repeated, and when the scanning has been completed, the image drawing process is ended (Step S210).

According to the optical scanning image forming method of this embodiment, image distortion can be corrected by a simple technique. Further, the method of this embodiment eliminates the need to store, in a memory, an actual pattern or a reference chart obtained by PSD. Further, this embodiment allows for correction as long as a plurality of images can be obtained, and thus, in a case of a scanning endoscope for example, distortion can be corrected with the scanning endoscope being in the test subject. In addition, correction can be made in a use environment, which makes the apparatus to be readily adaptable to environmental changes such as temperature.

As has been described above with reference to the embodiment, the disclosed optical scanning image forming apparatus and optical scanning image forming method are applied to an image forming technology including a plurality of light scanning patterns that are different in scanning direction and rate of light. In particular, the disclosed apparatus and method are applicable to any optical scanning technology that involves technical problems which may momentarily or chronologically generate a behavior different from the scanning pattern that has been planned in one frame or between a plurality of frames. Therefore, the disclosed apparatus and method should no way be limited to the aforementioned embodiment. For example, the plurality of different scanning patterns may employ raster scan. This case may employ two scanning patterns, which may be, for example, mutually opposite in the fast axis direction and mutually the same in the low axis direction. Alternatively, the plurality of different scanning patterns may employ Lissajous scan. This case may employ, for example, two scanning patterns that have, for example, line symmetric loci in plan view. The actuators may employ, for example, an electromagnetic method for vibrating an optical fiber provided with a magnetic body, without being limited to the piezoelectric method using piezoelectric elements as described above. Further, for example, the aforementioned embodiment employs the image construction coordinates calculator/distortion correction data calculator 52 which is capable of both calculating image construction coordinates and calculating distortion correction data, which however may be included as two separate functional parts. In addition, various alterations and modifications are available without departing from the gist of the disclosure. The distortion correction data stored in a memory may be configured to be compared for each round and/or each frame and displayed on a display part in forms (of, for example, drawings, values, and graphs) that would help to understand the variations thereof, to thereby allow for confirming and analyzing the scanning condition at any time.

REFERENCE SIGNS LIST 1 optical scanning image forming apparatus
2 light source section
3 illumination scanning section
4 light detection section
5 calculation section
6 image drawing section
7 display part

What is claimed is:

1. An optical scanning image forming apparatus, comprising:
    a light source section;
    an illumination scanning section scanning illumination light from the light source section and irradiating the illumination light onto an object;

a light detection section detecting detection light from the object;

a calculation section calculating: a drive waveform for providing a light scanning pattern to be formed by the illumination scanning section; and image construction coordinates; and an image drawing section drawing an image, based on the detection light detected by the light detection section and the image construction coordinates, wherein the calculation section provides a plurality of different light scanning patterns to the illumination scanning section, and compares between data on the detection light detected by the light detection section when the illumination light has been scanned in the plurality of different scanning patterns, to thereby calculate distortion correction data.

2. The optical scanning image forming apparatus according to claim 1, wherein the plurality of different light scanning patterns are different in light scanning direction.

3. The optical scanning image forming apparatus according to claim 1, wherein the plurality of different light scanning patterns have portions opposite in scanning direction of the illumination light.

4. The optical scanning image forming apparatus according to claim 1, wherein the plurality of different light scanning patterns are each in a spiral shape and include two scanning patterns having distortions mutually opposite in the rotational direction.

5. The optical scanning image forming apparatus according to claim 4, wherein the calculation section compares between data on the detection light detected by the light detection section when the illumination light has been scanned in the two scanning patterns, to thereby calculate distortion correction data.

6. The optical scanning image forming apparatus according to claim 4, wherein the calculation section takes out data sequences of the illumination light detected by the light detection section for a certain period when the illumination light has been scanned in the two scanning patterns, and aligns the two data sequences with one of the data sequences that has been obtained for one of the two scanning patterns being converted in an opposite direction and aligned such that the difference between the converted data sequence and the data sequence of the illumination light scanned in the other scanning pattern are minimized, to thereby calculate the distortion correction data based on comparison between the two data sequences.

7. The optical scanning image forming apparatus according to claim 1, wherein the image drawing section uses the distortion correction data to correct, in the scanning of the illumination light after the distortion correction data has been calculated, data on the detection light detected by the light detection section, and draws an image.

8. The optical scanning image forming apparatus according to claim 1, wherein the plurality of different scanning patterns are raster scans and use scanning patterns mutually opposite in a fast axis direction.

9. An optical scanning image forming method, comprising the steps of:

providing a plurality of different light scanning patterns to an illumination scanning section which scans illumination light from a light source section to irradiate an object with the illumination light; and causing a calculation section to calculate distortion correction data based on comparison between data on detection light detected by a light detection section when the illumination light has been scanned in the plurality of different scanning patterns.

10. The optical scanning image forming method according to claim 9, wherein the plurality of different light scanning patterns are different in the scanning direction of the illumination light.

11. The optical scanning image forming method according to claim 9, wherein the plurality of different light scanning patterns have a portion opposite in scanning direction of the illumination light.

12. The optical scanning image forming method according to claim 9, wherein the plurality of different scanning patterns are each in a spiral shape, and include two scanning patterns mutually opposite in distortion in the rotational direction.

13. The optical scanning image forming method according to claim 12, wherein the calculation section calculates distortion correction data based on comparison between data on the detection light detected by the light detection section, when the illumination light has been scanned in the two scanning patterns.

14. The optical scanning image forming method according to claim 13, wherein the distortion correction data is a data sequence for each round of a spiral scanning pattern.

15. The optical scanning image forming method according to claim 12, wherein the calculation section takes out data sequences of the detection light detected by the light detection section for a certain period when the illumination light has been scanned in the two scanning patterns, and aligns the two data sequences with one of the data sequences that has been obtained for one of the two scanning patterns being converted in an opposite direction and aligned such that the difference between the converted data sequence and the data sequence of the illumination light scanned in the other scanning pattern are minimized, to thereby calculate the distortion correction data based on comparison between the two data sequences.

16. The optical scanning image forming method according to claim 9, further comprising, in scanning of the illumination light after the step of calculating the distortion correction data, the step of causing the image drawing section to use the distortion correction data to correct data on the detection light detected by the light detection section, and to draw an image.

17. The optical scanning image forming method according to claim 9, wherein the plurality of different scanning patterns are raster scans, and use scanning patterns mutually opposite in a fast axis direction.

* * * * *